United States Patent [19]

Yabusaki

[11] Patent Number: 4,738,932

[45] Date of Patent: Apr. 19, 1988

[54] REAGINIC TEST FOR SYPHILIS

[75] Inventor: Kenichi K. Yabusaki, Albany, Calif.

[73] Assignee: Advanced Polymer Systems, Inc., Redwood City, Calif.

[21] Appl. No.: 804,059

[22] Filed: Dec. 3, 1985

[51] Int. Cl.$^4$ ................. G01N 33/571; G01N 33/543; G01N 33/549

[52] U.S. Cl. ................................ 436/511; 436/518; 436/532; 436/533; 436/534; 436/808; 436/811; 435/5; 435/181; 435/810

[58] Field of Search ............... 436/511, 532, 533, 534, 436/518, 808, 811; 435/188, 5, 7, 810

[56] References Cited

U.S. PATENT DOCUMENTS

| | | | |
|---|---|---|---|
| 3,564,089 | 2/1971 | Kiddy | 436/534 X |
| 3,720,760 | 3/1973 | Bennich et al. | 436/532 X |
| 4,181,636 | 1/1980 | Fischer | 260/8 |
| 4,218,335 | 8/1980 | Mochida et al. | 436/533 X |
| 4,226,847 | 10/1980 | Ogasa et al. | 436/534 X |
| 4,264,766 | 4/1981 | Fischer | 536/51 |
| 4,272,510 | 6/1981 | Smith et al. | 427/47 |
| 4,572,901 | 2/1986 | Ceriani et al. | 436/528 |

OTHER PUBLICATIONS

Rubin et al., "J. of Immunol. Methods" 63 (1983), pp. 359–366.
Uyeda, C. T., American Journal of Clinical Pathology (1963) 40:329–333.
Manual of Tests for Syphilis, U.S. Dept. of Health, Education, and Welfare (1969), pp. 23–26, 33–42.
Larsen, S. A., Current Status of Laboratory Tests for Syphilis (1983), pp. 162–170.
Pettit, D. E., et al., Journal of Clin. Microbiol. (1983), 18:1141–1145.

*Primary Examiner*—Christine M. Nucker
*Attorney, Agent, or Firm*—Ciotti & Murashige, Irell & Manella

[57] ABSTRACT

A reaginic agglutination test for syphilis-associated antibodies is disclosed. The test uses an antigen reagent that comprises a buffered aqueous suspension of cardiolipin antigen ionically coupled to latex particles via a polypeptide bridge. Positive sera react with the antigen reagent and yield an agglutination pattern characterized by medium to large aggregates. Negative sera yield no agglutinated particles.

25 Claims, No Drawings

REAGINIC TEST FOR SYPHILIS

DESCRIPTION

1. Technical Field

This invention is in the field of immunological testing. More particularly, it concerns a screening test for syphilis-associated antibodies that employs cardiolipin antigen ionically coupled to latex particles via a polypeptide bridge.

2. Background Art

Two main categories of serologic tests for syphilis are available: tests for reaginic antibody and tests for treponemal antibody. Reaginic tests use cardiolipin as antigen and are normally used for screening because they are sensitive and fast, but lack a high degree of specificity. The treponemal tests use treponemal antigens and, because they involve a more rigorous and demanding procedure, are used principally as confirmatory tests on samples that are positive in the reaginic test.

Commercial reaginic tests are divided into two categories: microscopic and macroscopic. The microscopic tests are the Venereal Disease Research Laboratory (VDRL) slide and the Unheated Serum Reagin (USR) tests. The VDRL antigen consists of an ethanol solution of 0.03% cardiolipin, 0.9% cholesterol, and 0.21% lecithin. VDRL antigen is added to buffered saline containing 0.05% formaldehyde to form a suspension of VDRL antigen. The antigen suspension is then added to heat-treated (56° C. for 30 min) serum. If the serum contains reaginic antibodies, they will combine with the antigen to form a flocculant that is visible on microscopic examination. Lack of flocculation is a negative reaction. The USR is a flocculation test similar to the VDRL. It differs from the VDRL in that is uses a VDRL antigen suspension stabilized with ethylene diamine tetraacetic acid with choline chloride added and does not require serum heating.

There are several macroscopic reagin tests. Most of them involve a modified VDRL antigen that provides a macroscopically visible antigen-antibody reaction product. Examples of such modifiers are charcoal particles and dyes such as Sudan Black B and toluidine red.

Uyeda, C. T., *Am J Clin Path* (1963) 40: 329–333, describes a macroscopic reagin test that uses VDRL antigen adsorbed onto latex particles. Both unheated and heated sera were tested, but the results with unheated sera were characterized as being occasionally inconsistent.

Some treponemal tests use treponemal antigen immobilized on a carrier. For instance, the *Treponema pallidum* hemagglutination test (TPHA) uses red blood cells as a carrier with treponemes adsorbed on their surfaces. Also, U.S. Pat. No. 4,272,510 describes an enzyme immunoassay for antibodies to *Treponema pallidum* that uses treponemal antigen immobilized on ferrous metal beads.

U.S. Pat. No. 4,181,636 suggests that various "immunologically active materials", including *Treponema pallidum*, may be covalently bound to carboxylated latex particles via a coupling agent such as a carbodiimide. U.S. Pat. No. 4,264,766 suggests a similar system in which antigen is bound to the carboxylated latex via a polysaccharide.

DISCLOSURE OF THE INVENTION

The present invention provides a test for syphilis-associated antibodies that combines the sensitivity (lack of false-negatives), speed, and simplicity of existing reagin tests with the advantages of not requiring use of heat inactivated serum and being useful for testing plasma and cerebrospinal fluid as well as serum. It is also more sensitive than the VDRL test.

A critical and novel antigen reagent is the cornerstone of the test. It comprises a stable aqueous suspension of cardiolipin antigen ionically coupled to latex particles via a polypeptide bridge. This reagent is used in a flocculation or agglutination type assay that includes the following steps: (1) incubating a test sample suspected of containing syphilis-associated antibodies with the antigen reagent under conditions that permit reaction between any such antibody in the sample and the cardiolipin antigen component of the reagent, and (2) determining whether an agglomerate or flocculant has formed.

The reagent will normally be sold as part of a kit for conducting the above-described assay. The kit comprises in packaged combination: (a) a first container that contains the antigen reagent; (b) a second container that contains a negative control sample that does not react with the antigen reagent; and (c) a third container that contains a positive control sample that reacts with the antigen reagent and forms a visible flocculant or agglomerated reaction product. The kit will also typically contain a suitable buffer for diluting samples and instructions for carrying out the test.

Modes for Carrying Out the Invention

The test sample may be serum, plasma, or cerebrospinal fluid. These test samples may be obtained by conventional collection and processing procedures. In the case of serum, blood is obtained by venipuncture, allowed to clot, and serum is removed. Serum from a person infected with *Treponema pallidum* contains syphilitic reagin (a mixture of antibodies formed by the host in response to lipoidal material released from damaged host cells early in the infection that react with sensitized cardiolipin) and specific antibodies to treponemal antigen. Syphilitic reagin is sometimes referred to herein as "syphilis-associated antibodies".

The antigen reagent of the invention is made by ionically coupling cardiolipin antigen to latex particles via a polypeptide bridge. Preferably, a positively charged polypeptide is first bound to latex particles either by passive adsorption or chemical (covalent or ionic) bonds. In passive adsorption the latex may be neutral, carboxylated, or amino-modified whereas in chemical bonding the surface of the latex will be modified with coupling agents such as carbodiimides, in a manner that permits chemical bonding between the polypeptide bridging agent and the surface of the latex.

The positively charged polypeptide may be a homopolymer, such as a polycationic polyamino acid (e.g., polylysine, polyarginine) or composed of varying amino acids, such as methylated serum albumin. Correlatively, the polypeptide may be composed solely of amino acids or include various substituents such as sugar moieties, acyl groups, and the like. The weight average molecular weight of the polypeptide will typically be below about 500,000, preferably below about 100,000.

The particle size of the latex will usually be in the range of 0.1 to 15 microns, more usually 0.1 to 7 microns. A preferred latex has a particle size of 0.4 to 0.8 microns. Neutral and modified latexes for use in making the antigen complex are available commercially.

The latex particles are contacted with an aqueous solution of the polypeptide at a particle concentration that does not result in very large particle aggregates. In the case of the particles described in the examples, infra, a particle concentration in the final volume of about 4 mg/ml was found to be optimum. A saturation concentration of polypeptide in the solution is preferred.

The cardiolipin antigen that is coupled to the latex is in the form of an ethanolic solution of cardiolipin (a diphosphatidylglycerol purified from beef heart) combined with cholesterol and lecithin or other sensitizing agents that enable cardiolipin to react with syphilitic reagin. The ethanolic solution of cardiolipin and lecithin and cholesterol will contain cardiolipin in the range of approximately 0.01 to 5 mg/ml, more usually 0.1 to 1 mg/ml, and most preferably 0.2 to 0.5 mg/ml, and lecithins (from hen egg yolk, soybean, or synthetic) in the range of approximately 0.04 to 12 mg/ml, more ususually 0.5 to 4 mg/ml, and most preferably approximately 1.5 to 2.5 mg/ml, and cholesterol in the range of approximately 0.5 to 13 mg/ml, usually 5 to 11 mg/ml, and preferably 8 to 9 mg/ml. VDRL antigen (described above) is preferred.

The resulting latex particle-polypeptide-cardiolipin antigen complex is suspended in an aqueous medium buffered to a pH in the range of 5–10, usually 5.5 to 8.0, and preferably 6.0 to 7.0. The concentration of complex in the medium will be in the range of about 0.01 to 4 mg/ml, usually 0.1 to 2 mg/ml, and preferably 0.3 to 0.9 mg/ml. Various buffers may be used such as Tris, glycine, and phosphate. Phosphate is preferred. The concentration of buffer will generally be in the range of approximately 0.0001 to 0.05M, more usually in the range of approximately 0.00075 to 0.003M. The buffer will contain a salt such as sodium chloride. The sodium chloride concentration in the buffer will generally be in the range of approximately 0.01 to 0.5M, more usually in the range of approximately 0.05 to 0.2M, and preferably approximately 0.16 to 0.18M.

Other additives may also be in the buffer medium which are employed for preserving or protecting individual components or reagents or for aiding the performance characteristics of the test. Particularly, formaldehyde can be employed in amounts of approximately 0.01 to 0.5 volume percent, more usually approximately 0.02 to 0.1 volume percent, and preferably approximately 0.04 to 0.06 volume percent. Ethylenediaminetetraacetic acid (EDTA) can be employed in amounts of approximately 0.1 to 1.0 volume percent, more usually approximately 0.2 to 0.7 volume percent and preferably approximately 0.3 to 0.6 volume percent. Choline chloride can be employed in amounts of approximately 2.5 to 15 volume percent, more usually approximately 5 to 13 volume percent and preferably approximately 8 to 11 volume percent. Sodium azide can be employed in amounts of approximately 0.005 to 0.1 volume percent. Thimerosal can be employed in amounts of approximately 0.005 to 0.1 volume percent.

Dyes may be incorporated into the latex particles and/or cardiolipin antigen to facilitate visualization of the agglomerate in the reading phase of the test. If a dye is incorporated into the cardiolipin, it should be lipophilic so that is does not leach into the aqueous phase. Examples of such dyes are Sudan black and Nile red.

The invention test is a two-step procedure in which the test sample is first incubated with the antigen reagent. The incubation may be carried out in conventional agglutination slides or Brewers cards with 18 mm circles under conditions that favor antigen-antibody binding (essentially physiological pH, temperature, and ionic strength). The mixture is agitated gently to promote reaction (binding) between any syphilis-associated antibodies in the test serum and the antigen component of the antigen reagent. Relatively short incubation periods on the order of 4 to 12 minutes are sufficient. Longer times may be used for convenience. Negative and positive control samples are run in parallel with test sample(s) for comparison purposes.

After the incubation step, the results of the test may be read visually by placing the slide on a slide viewer and examining the contents of the slide wells for agglutination pattern under indirect light. A negative pattern shows no agglutinated particles. A weakly positive pattern is characterized by the distinct presence of slightly grainy to small agglutinated particles. A positive pattern is scored by the presence of medium to large agglutinated particles.

The invention is further illustrated by the following examples. These examples are not intended to limit the invention in any manner.

EXAMPLES

A. Preparation of Methylated Bovine Serum Albumin-Carboxylated Latex

To approximately 86 mg of carboxylated latex particles (0.4–0.6 microns) suspended in 1 ml of distilled deionized water is added 5 ml of a methylated bovine serum albumin solution at 4.1 mg/ml in 0.25 Molar glycine-buffered saline followed immediately by the addition of 15.5 ml of 0.25 Molar glycine-buffered saline. The entire mixture is gently stirred for 15 min, then placed in a water bath set at 37±1° C. for 2 hr, then placed at 4° C. overnight. The entire suspension is then centrifuged at 10,000 rpm in a microcentrifuge for 10 min or at full speed on table top clinical centrifuge for 10–15 min to sediment the methylated bovine serum albumin-adsorbed latex particles. The supernatant is carefully removed and the pellet is resuspended in a phosphate-buffered saline pH 6.0 and recentrifuged at 10,000 rpm for 10 min or at full speed on table top clinical centrifuge for 10–15 min. The supernatant is carefully removed and the resultant pellet of methylated bovine serum albumin-adsorbed carboxylated latex particles resuspended in phosphate-buffered saline, pH 6.0, and brought to a final volume of approximately 10 ml. This suspension of particles constituted a stock suspension from which subsequent reagents were prepared.

B. Preparation of Methylated Bovine Serum Albumin Carboxylated Latex Cardiolipin Antigen Reagent To approximately 2.15 mg of methylated bovine serum albumin carboxylated latex particles suspended in 0.4 ml of phosphate-buffered saline, pH 6.0, and contained in a 25 ml capacity cylindrical vial is added, dropwise with gentle shaking of the vial, 0.5 ml of an ethanolic solution consisting of approximately 0.03% cardiolipin, 0.21% lecithin, and 0.9% cholesterol. After the final drop of the ethanolic cardiolipin/lecithin/cholesterol solution is added, 4.1 ml of phosphate-buffered saline, pH 6.0, is added to the milky white suspension and the entire suspension gently shaken in a rotary motion for 30 sec. The resultant methylated bovine serum albumin carboxylated latex cardiolipin antigen reagent is stored at 4° C.

C. Preparation of Poly-DL-Lysine Carboxylated Latex

To approximately 8.6 mg of carboxylated latex particles suspended in 1.8 ml of 0.25M glycine buffered saline, pH 8.2, is added 0.1 ml of a poly-DL-lysine (M.W. average 57,000) at 10 mg/ml in distilled water. The suspension is gently stirred for 15 min at room temperature, then placed in a 37±1° C. water bath for 2 hr followed by overnight incubation at 4° C. The poly-DL-lysine adsorbed carboxylated latex particles are centrifuged at 10,000 rpm in a microcentrifuge for 10 min and the resultant pellet resuspended in phosphate-buffered saline, pH 6.0, to a final latex particle concentration of approximately 16 mg/ml.

D. Preparation of Poly-DL-Lysine Carboxylated Latex Cardiolipin Antigen Reagent To approximately 2.15 mg of poly-DL-lysine carboxylated latex particles suspended in 0.4 ml of phosphate buffered saline, pH 6.0, and contained in a 25 ml capacity cylindrical vial is added, dropwise with gentle shaking of the vial, 0.5 ml of an ethanolic solution consisting of approximately 0.03% cardiolipin, 0.21% lecithin, and 0.9% cholesterol. After the final drop of the ethanolic cardiolipin/lecithin/cholesterol solution is added, 4.1 ml of phosphate-buffered saline, pH 6.0, is added to the milky white suspension and the entire suspension gently shaken in a rotary motion for 30 sec. The resultant poly-DL-lysine carboxylated latex cardiolipin reagent is stored at 4° C.

E. Preparation of Sudan Black B Carboxylated Latex Particles

To approximately 86 mg of carboxylated latex particles suspended in 1 ml of distilled water and placed under magnetic stirring is added dropwise 0.4 ml of an ethanolic solution of Sudan Black B at 2 mg/ml. The suspension is allowed to stir at room temperature for 2 hr, then the suspension is centrifuged at 10,000 rpm for 30 min in a microcentrifuge. The resultant pellet is resuspended in phosphate-buffered saline, pH 6.0, and recentrifuged as described above. This step is repeated until the supernatant is clear and free of visible dye.

F. Preparation of Methylated Bovine Serum Albumin Sudan Black B Carboxylated Latex Particles To approximately 17 mg of Sudan Black B carboxylated latex suspended in 0.2 ml of deionized distilled water is added 1 ml of a methylated bovine serum albumin solution at 4.1 mg/ml in 0.25M glycine-buffered saline, pH 8.2 followed immediately by the addition of 3.05 ml of 0.25 Molar glycine-buffered saline. After gentle mixing the suspension is allowed to incubate at 37±1° C. for 2 hr followed by an overnight incubation at 4° C. The suspension is centrifuged at 10,000 rpm in a microcentrifuge for 10 min and the resultant pellet resuspended in phosphate-buffered saline, pH 6.0, to a final latex particle concentration of approximately 17 mg/ml. The resultant methylated bovine serum albumin Sudan Black B carboxylated latex particle suspension is stored at 4° C.

G. Preparation of a Colored Methylated Bovine Serum Albumin Carboxylated Latex Cardiolipin Reagent To approximately 2.15 mg of methylated bovine serum albumin carboxylated latex particles or 2.15 mg of methylated bovine serum albumin Sudan Black B carboxylated latex particles suspended in 0.4 ml of phosphate-buffered saline, pH 6.0, and contained in a 25 ml capacity cylindrical vial is added, dropwise with gentle shaking of the vial, 0.5 ml of an ethanolic solution consisting of 0.03% cardiolipin, 0.21% lecithin, 0.9% cholesterol, and 0.07% Sudan Black B. after the final drop of the ethanolic cardiolipin/lecithin/cholesterol/Sudan Black B solution is added, 4.1 ml of phosphate-buffered saline, pH 6.0, is added to the dark bluish suspension and the entire suspension gently shaken in a rotary motion for 30 sec then left to stand at 4° C. for 18–24 hr. The entire suspension is mixed thoroughly and centrifuged at full speed in a table top clinical centrifuge for 10 min. After carefully decanting the supernatant, the resultant pellet is resuspended to the approximate original volume with phosphate-buffered saline, pH 6.0. The resultant dyed methylated bovine serum albumin carboxylated latex cardiolipin antigen reagent provides an antigen reagent which can be used to detect reaginic antibodies in serum, plasma, or spinal fluid or dilutions of serum, plasma, or spinal fluid by carrying out the antigen antibody reaction on, for example, a Brewer diagnostic 18 mm circle card. A positive test for reagin antibodies in serum or plasma or spinal fluid is indicated by blue agglutinated particles viewed against the white background of the card.

H. Test Procedure for Detecting Reaginic Antibodies in Unheated Serum

Approximately 0.1 ml of unheated serum is pipetted into a well of a plastic serological rotator slide measuring 0.2×5×7.5 cm containing 15 wells measuring 15 mm in diameter and 1 mm in depth. Then approximately 0.02 ml of methylated bovine serum albumin carboxylated latex cardiolipin antigen reagent is added to the serum sample. The slide is placed on the platform of a serological rotator and rotated at a constant speed of, for example, approximately 180 revolutions per minute for approximately four minutes. The slide is placed on the glass platform of a Hyperion Viewer with magnifier and examined under indirect light. A similar procedure is employed for testing cerebrospinal fluid.

I. Quantitative Reaginic Antibody Test

Prepare unheated serum, plasma, or cerebrospinal fluids as follows:
a. Pipette 0.2 ml of phosphate-buffered saline, pH 6.0, into each of five or more test tubes.
b. Add 0.2 ml of unheated serum, plasma, or spinal fluid to tube one, mix well, and transfer 0.2 ml to tube two.
c. Continue mixing and transferring 0.2 ml from one tube to the next until the last tube is reached. The respective dilution should be 1:2, 1:4, 1:8, 1:16, 1:32, etc.

Test each serum, plasma, or spinal fluid dilution and undiluted serum, plasma, or spinal fluid as described under H, "Test Procedure for Detecting Reaginic Antibodies in Unheated Serum".

The following table presents data on tests of clinical sera of known reactivity using the invention test and the VDRL.

| Sample | VDRL Dilution | | | | | | | Invention Dilution | | | | | | | |
| --- | --- | --- | --- | --- | --- | --- | --- | --- | --- | --- | --- | --- | --- | --- | --- |
| No. | 0 | 1:2 | 1:4 | 1:8 | 1:16 | 1:32 | 1:64 | 0 | 1:2 | 1:4 | 1:8 | 1:16 | 1:32 | 1:64 | 1:128 |
| 3392 | N | N | N | | | | | N | N | N | | | | | |
| 94 | R | R | R | W | N | N | | R | R | R | W | N | N | | |
| 3403 | W | N | N | | | | | W | N | N | | | | | |
| 3567 | R | R | R | R | W | N | N | R | R | R | R | W | N | | |
| 69 | W | N | N | | | | | W | W | W | N | N | | | |
| 90 | W | N | N | | | | | N | N | N | | | | | |
| 3601 | R | N | N | | | | | W | N | N | | | | | |
| 21 | R | W | N | | | | | W | N | N | | | | | |
| 22 | N | N | N | | | | | N | N | N | | | | | |
| 26 | W | N | N | | | | | W | N | N | | | | | |
| 27 | W | N | N | | | | | N | N | N | | | | | |
| 31 | R | R | R | R | W | N | | R | R | R | R | W | N | N | |
| 40 | R | W | N | | | | | R | R | W | N | N | N | | |
| 43 | W | N | N | | | | | N | N | N | | | | | |
| 82 | N | N | N | | | | | N | N | N | | | | | |
| 83 | N | N | N | | | | | N | N | N | | | | | |
| 85 | R | R | W | N | N | | | R | R | W | N | N | N | | |
| 3720 | R | R | R | R | W | N | | R | R | R | R | W | N | N | |
| 42 | N | N | N | | | | | N | N | N | | | | | |
| 45 | R | R | R | W | N | | | R | R | R | W | N | | | |
| 50 | W | N | N | | | | | N | N | N | | | | | |
| 55 | R | R | R | W | N | N | | R | R | R | R | N | N | | |
| 64 | R | R | R | W | N | N | | R | R | R | W | N | N | | |
| 3769 | W | N | N | | | | | N | N | N | | | | | |
| 97 | N | N | N | | | | | N | N | N | | | | | |
| 98 | N | N | N | | | | | N | N | N | | | | | |
| 3827 | R | W | N | | | | | R | W | N | N | N | N | | |
| 34 | R | R | R | R | W | N | | R | R | R | R | R | W | N | |

N = nonreactive, W = weakly reactive, R = strong reactive

Modifications of the above-described modes for carrying out the invention that are obvious to those of skill in the fields of immunological testing, medicine, and related fields are intended to be within the scope of the following claims.

I claim:

1. An antigen reagent for use in a reaginic test for syphilis comprising an aqueous suspension of cardiolipin antigen ionically coupled to latex particles via a positively charged polypeptide bridge.

2. The reagent of claim 1 wherein the latex particles are neutral or modified to have negatively charged or reactive surface moieties.

3. The reagent of claim 1 wherein the particle size of the latex is in the range of 0.1 to 7 microns.

4. The reagent of claim 1 wherein the particle size of the latex is in the range of 0.4 to 0.8 microns.

5. The reagent of claim 1 wherein the polypeptide is a polycationic polyamino acid.

6. The reagent of claim 1 wherein the polypeptide is polylysine.

7. The reagent of claim 1 wherein the cardiolipin antigen is an ethanol solution of 0.03% cardiolipin, 0.9% cholesterol and 0.21% lecithin.

8. The reagent of claim 1 wherein the aqueous suspension is buffered to a pH in the range of 5-10.

9. The reagent of claim 1 wherein the aqueous suspension is buffered at a pH of 6.0 to 7.0.

10. The reagent of claim 1 wherein the particle size of the latex is in the range of 0.4 to 0.8 microns, the latex is a carboxylated latex, the polypeptide bridge is a methylated serum albumin or polylysine bridge, the cardiolipin antigen is an ethanol solution of 0.03% cardiolipin, 0.9% cholesterol and 0.21% lecithin, the suspension is buffered to a pH of 6.0 to 6.5, and the concentration of cardiolipin antigen ionically coupled to latex particles via a polypeptide bridge in the suspension is 0.3 to 0.9 mg/ml.

11. A reaginic test for syphilis-associated antibodies comprising:
 (a) incubating a sample suspected of containing said antibodies with the antigen reagent of claim 1 under conditions that permit binding between said antibodies and antigen in said antigen reagent; and
 (b) determining whether the antigen reagent has agglutinated, agglutination indicating the presence of said antibodies in said sample.

12. A reaginic test for syphilis-associated antibodies comprising:
 (a) incubating a sample suspected of containing said antibodies with the antigen reagent of claim 5 under conditions that permit binding between said antibodies and antigen in said antigen reagent; and
 (b) determining whether the antigen reagent has agglutinated, agglutination indicating the presence of said antibodies in said sample.

13. A serologic test for syphilis-associated antibodies comprising:
 (a) incubating a sample suspected of containing said antibodies with the antigen reagent of claim 6 under conditions that permit binding between said antibodies and antigen in said antigen reagent; and
 (b) determining whether the antigen reagent has agglutinated, agglutination indicating the presence of said antibodies in said sample.

14. A serologic test for syphilis-associated antibodies comprising:
 (a) incubating a sample suspected of containing said antibodies with the antigen reagent of claim 7 under conditions that permit binding between said antibodies and antigen in said antigen reagent; and
 (b) determining whether the antigen reagent has agglutinated, agglutination indicating the presence of said antibodies in said sample.

15. A serologic test for syphilis-associated antibodies comprising:

(a) incubating a sample suspected of containing said antibodies with the antigen reagent of claim 8 under conditions that permit binding between said antibodies and antigen in said antigen reagent; and (b) determining whether the antigen reagent has agglutinated, agglutination indicating the presence of said antibodies in said sample.

16. A serologic test for syphilis-associated antibodies comprising:

(a) incubating a sample suspected of containing said antibodies with the antigen reagent of claim 10 under conditions that permit binding between said antibodies and antigen in said antigen reagent; and (b) determining whether the antigen reagent has agglutinated, agglutination indicating the presence of said antibodies in said sample.

17. A kit for conducting a serologic test for syphilis-associated antibodies comprising, in packaged combination:

(a) a first container containing the antigen reagent of claim 1;

(b) a second container containing a negative control sample of serum, plasma, or cerebrospinal fluid that does not react with the antigen reagent; and (c) a third container containing a positive control sample of serum, plasma, or cerebrospinal fluid that reacts with the antigen reagent.

18. A kit for conducting a serologic test for syphilis-associated antibodies comprising, in packaged combination:

(a) a first container containing the antigen reagent of claim 5;

(b) a second container containing a negative control sample of serum, plasma, or cerebrospinal fluid that does not react with the antigen reagent; and (c) a third container containing a positive control sample of serum, plasma, or cerebrospinal fluid that reacts with the antigen reagent.

19. A kit for conducting a serologic test for syphilis-associated antibodies comprising, in packaged combination:

(a) a first container containing the antigen reagent of claim 6;

(b) a second container containing a negative control sample of serum, plasma, or cerebrospinal fluid that does not react with the antigen reagent; and (c) a third container containing a positive control sample of serum, plasma, or cerebrospinal fluid that reacts with the antigen reagent.

20. A kit for conducting a serologic test for syphilis-associated antibodies comprising, in packaged combination:

(a) a first container containing the antigen reagent of claim 7;

(b) a second container containing a negative control sample of serum, plasma, or cerebrospinal fluid that does not react with the antigen reagent; and (c) a third container containing a positive control sample of serum, plasma, or cerebrospinal fluid that reacts with the antigen reagent.

21. A kit for conducting a serologic test for syphilis-associated antibodies comprising, in packaged combination:

(a) a first container containing the antigen reagent of claim 8;

(b) a second container containing a negative control sample of serum, plasma, or cerebrospinal fluid that does not react with the antigen reagent; and (c) a third container containing a positive control sample of serum, plasma, or cerebrospinal fluid that reacts with the antigen reagent.

22. A kit for conducting a serologic test for syphilis-associated antibodies comprising, in packaged combination:

(a) a first container containing the antigen reagent of claim 10;

(b) a second container containing a negative control sample of serum, plasma, or cerebrospinal fluid that does not react with the antigen reagent; and (c) a third container containing a positive control sample of serum, plasma, or cerebrospinal fluid that reacts with the antigen reagent.

23. The reagent of claim 1 wherein the polypeptide is methylated serum albumin.

24. A reaginic test for syphilis-associated antibodies comprising:

(a) incubating a sample suspected of containing said antibodies with the antigen reagent of claim 23 under conditions that permit binding between said antibodies and antigen in said antigen reagent; and (b) determining whether the antigen reagent has agglutinated, agglutination indicating the presence of said antibodies in said sample.

25. A kit for conducting a serologic test for syphilis-associated antibodies comprising, in packaged combination:

(a) a first container containing the antigen reagent of claim 23;

(b) a second container containing a negative control sample of serum, plasma, or cerebrospinal fluid that does not react with the antigen reagent; and (c) a third container containing a positive control sample of serum, plasma, or cerebrospinal fluid that reacts with the antigen reagent.

* * * * *